(12) United States Patent
Baumann et al.

(10) Patent No.: US 10,441,184 B2
(45) Date of Patent: Oct. 15, 2019

(54) ELECTROCARDIOGRAM DEVICE AND METHODS

(71) Applicants: Eric Baumann, San Diego, CA (US); Lev Korzinov, San Diego, CA (US); David Churchville, San Diego, CA (US)

(72) Inventors: Eric Baumann, San Diego, CA (US); Lev Korzinov, San Diego, CA (US); David Churchville, San Diego, CA (US)

(73) Assignee: VENTRILINK CORPORATION, San Diego, CA (US)

( * ) Notice: Subject to any disclaimer, the term of this patent is extended or adjusted under 35 U.S.C. 154(b) by 0 days.

(21) Appl. No.: 15/460,036

(22) Filed: Mar. 15, 2017

(65) Prior Publication Data

US 2017/0265765 A1    Sep. 21, 2017

Related U.S. Application Data

(60) Provisional application No. 62/309,292, filed on Mar. 16, 2016, provisional application No. 62/361,374, filed on Jul. 12, 2016.

(51) Int. Cl.
| | |
|---|---|
| *A61B 5/00* | (2006.01) |
| *A61B 5/04* | (2006.01) |
| *A61B 5/046* | (2006.01) |
| *A61B 5/044* | (2006.01) |
| *A61B 5/0428* | (2006.01) |

(52) U.S. Cl.
CPC .......... *A61B 5/04012* (2013.01); *A61B 5/044* (2013.01); *A61B 5/046* (2013.01); *A61B 5/726* (2013.01); *A61B 5/7257* (2013.01); *A61B 5/7264* (2013.01); *A61B 5/7465* (2013.01); *A61B 5/002* (2013.01); *A61B 5/0428* (2013.01)

(58) Field of Classification Search
CPC ... A61B 5/04012; A61B 5/046; A61B 5/7257; A61B 5/726; A61B 5/7264
See application file for complete search history.

(56) References Cited

U.S. PATENT DOCUMENTS

| | | | |
|---|---|---|---|
| 5,704,365 | A | 1/1998 | Albrecht et al. |
| 5,819,007 | A | 10/1998 | Elghazzawi |
| 6,016,442 | A | 1/2000 | Hsu et al. |
| 6,418,340 | B1 | 7/2002 | Conley et al. |

(Continued)

OTHER PUBLICATIONS

Uspenskiy, V. Diagnostic System Based on the Information Analysis of Electrocardiograph, Mediterranean Conference on Embedded Computing, 2012.

(Continued)

*Primary Examiner* — William J Levicky
(74) *Attorney, Agent, or Firm* — Mark Wisnosky

(57) ABSTRACT

Devices and methods are described that provide improved diagnosis from the processing of physiological data. The methods include use of transforms prior to submitting the data to a multiple level neural network. In one embodiment for ECG analysis, a template is used to subtract data that is not pertinent to the diagnosis and then a Fourier transform is applied to the time series data. Examples are shown with applications to electrocardiogram data, but the methods taught are applicable to many types of physiological data.

6 Claims, 9 Drawing Sheets

(56) References Cited

U.S. PATENT DOCUMENTS

| | | | |
|---|---|---|---|
| 6,463,320 | B1 | 10/2002 | Xue et al. |
| 7,058,444 | B2 | 6/2006 | Logan et al. |
| 7,142,907 | B2 | 11/2006 | Xue et al. |
| 7,263,399 | B2 | 8/2007 | Carlson |
| 8,433,399 | B1 | 4/2013 | Nosrati et al. |
| 8,478,389 | B1 * | 7/2013 | Brockway ............ A61B 5/0452 600/509 |
| 9,254,092 | B2 | 2/2016 | Albert et al. |
| 9,254,095 | B2 | 2/2016 | Galloway et al. |
| 9,268,876 | B2 | 2/2016 | MacInnis et al. |
| 9,277,871 | B2 | 3/2016 | Keenan et al. |
| 2006/0264769 | A1 | 11/2006 | Satin et al. |
| 2008/0109041 | A1 * | 5/2008 | de Voir ................ A61B 5/0452 607/7 |
| 2010/0268103 | A1 | 10/2010 | McNamara et al. |
| 2011/0166468 | A1 | 7/2011 | Prystowsky et al. |
| 2012/0071730 | A1 | 3/2012 | Romero |
| 2013/0096395 | A1 | 4/2013 | Katra et al. |
| 2013/0116585 | A1 | 5/2013 | Bouguerra |
| 2013/0184600 | A1 | 7/2013 | Tan et al. |
| 2015/0190067 | A1 | 7/2015 | Prystowsky et al. |
| 2015/0216426 | A1 * | 8/2015 | Burton ................ A61B 5/0468 600/509 |
| 2016/0000349 | A1 * | 1/2016 | Sullivan ............ A61B 5/0452 600/509 |

OTHER PUBLICATIONS

Dong, X. et al, Electrocardiogram (ECG) pattern modeling and recognition via deterministic learning, Control Theory Tech. vol. 12, No. 4 pp. 333-344, Nov. 2014.

Dmitrievich, I. A. Deep Learning in information analysis of electrocardiogram signals diagnostics, Masters Thesis, Moscow Institute of Physics and Technology, 2015.

Qiuzhen, X. Neural—Network -based Adaptive matched filtering for QRS Detection, IEEE Transactions on Biomedical Engineering, vol. 39, No. 4, Apr. 1992.

Cuiwei, L. et al. Detection of ECG Characterisitic Points using Wavelet Transforms, IEEE Transactions on Biomedical Engineeering, vol. 42, No. 1, Jan. 1995.

Priyadarshini, B. Determining ECG characteristics using wavelet transforms, International Journal of Engineering Research and Technology, vol. 1, Issue 6, Aug. 2012.

Hao, Y. et al. An efficient Wavelet—based Pattern matching scheme for ECG data compression, IEEE International Workshop in Biomedical Circuits and systems, 2004.

Zheng, Y. et al, Time Series Classification using Multi-channels Deep convolutional neural networks, Springer International Publishing, WAIM, 2014.

* cited by examiner

ELECTROCARDIOGRAM DEVICE AND METHODS

CROSS-REFERENCE TO RELATED APPLICATIONS

This Application claims priority to U.S. Provisional patent application No. 62/309,292, filed on 16 Mar. 2016, titled: Electrocardiogram Device and Methods, and U.S. Provisional patent application No. 62/361,374, filed on 12 Jul. 2016, titled: Electrocardiogram Device and Methods, both applications by the same inventors.

BACKGROUND OF THE INVENTION

Technical Field

The present invention relates to a health care device including physiological data acquisition and methods of analysis of the data and use for the device.

Related Background Art

As sensors for physiological data and data acquisition and data handling systems have improved, the amount of physiological data available to caregivers has expanded. It is now common practice to acquire data continuously from electronic sensors attached to patients. Nonlimiting examples of such sensors include temperature probes, probes sensitive to movement to detect breathing, sensors that detect electrical signals from the patient such as electroencephalograms (EEG) and electrocardiograms (ECG), sensors for chemistry such as blood oxygen detectors and blood glucose levels. The data is typically acquired versus time. The signal from the sensors is often a voltage or current measurement that is passed through an analog to digital converter to provide a numeric intensity measurement versus time. The analyses look for variations or patterns in the acquired data that are indicative of a disease or abnormal state. In many cases, such as that in the case of electroencephalogram and electrocardiogram data, the data represents repeating waveform patterns. The analysis uses filtering, transform techniques to extract waveform morphology, fundamental frequencies and patterns in the acquired data. The data may be acquired over periods of time from seconds to months. The sensors and data acquisition may be used for patients that are not moving, such as those confined to a bed and those in an intensive care unit of a hospital or the sensors may be attached to ambulatory patients and data is collected continuously as the patient moves about in their normal life routines.

A common feature of the data analysis for such physiological information is to look for anomalies that may have indicated either a disease state or a critical state where a caregiver intervention is required to aid the patient. The latter are common in intensive care unit situations. The large amount of data being acquired from a large number of patients has required the development of automated routines to evaluate the collected data. Frequently the analysis is used to provide automated response, such as in the case of insulin dosing systems responsive to automated blood glucose measurements or in the case of pace makers where an external electrical stimulus is provided upon detection of irregularity in the patient's heartbeat. The physiological data analysis is also frequently used to trigger alarms indicating immediate action is required, such as in an intensive care unit monitoring of an at risk patient. A common failure of all of these analyses and is that false alarms are common. It has been reported that in electrocardiogram data collected in an intensive care unit as much as 86% of the alarms were false alarms.

The data analysis typically involves looking for patterns in the data that are indicative of a disease or abnormal state. Automated algorithms are applied to measure for example in the case of an electrocardiogram, the heart rate, variations in the heart rate and shapes of the repeating waveforms. Algorithms are typically tested against a standard database of acquired data that includes cases where diagnoses of the state of the patients have been independently confirmed. Heretofore algorithms have been tested one at a time and optimized for accuracy and sensitivity to a particular condition. The goal has been to find a single algorithm that will provide the sensitivity and accuracy for all patients. No such algorithm has been found and indeed variations in patients and conditions make such a Holy Grail algorithm unlikely. Caution has dictated to set the sensitivity of the algorithm high, so as to not miss disease or emergency states. This procedure results in errors especially in the form of excessive false positive results for disease or emergency responses. Algorithms optimized for a database have been found on average when applied to individual patients to produce excessive errors that must be reconciled by a trained technician.

The current state of the art for detecting cardiac events in ambulatory patients involves either running a single algorithm on a patient attached device or running a single algorithm on servers that receive a full disclosure data stream from an ambulatory patient attached device. In some cases, a technician reviews every beat of one or two days of full disclosure ECG using a semi-automated algorithm that assists the technician in this review. Electrocardiogram data acquired over a period of days is typically referred to as a "Holter scan" and provides detailed information on the actual number of beats of each morphology, number of abnormal beats, and exact length and type of arrhythmic episodes. Ambulatory algorithms are typically tuned on a small data set to be as sensitive as practical on the entire patient population, and these performance numbers are published using a specific standard so that physicians can compare the performance of different algorithms on a standard small data sent constructed to reflect what the algorithm would encounter in the real world. This usually results in a large number of false positive events that a technician must deal with in order to get to acceptable levels of sensitivity. These false positive events require technician time to review and increase the cost of providing ambulatory monitoring services. In addition, device side algorithms or server side algorithms typically do not provide quantifiable beat counts as a Holter scan would. They also do not typically provide interpretive statements, which the technician applies after reviewing and possibly correcting the event presented by the algorithm.

Patients may also present with distinctly different cardiac signals depending on their disease state, the normal amplitude of the electrical activity of their heart, the orientation of their heart in their chest cavity and other idiosyncrasies provide challenges to detecting events with high specificity. Currently, a single algorithm must take into account all of the possible signals it may encounter from any patient in order for the algorithm to provide adequate sensitivity and diagnostic yield. This generally results in large numbers of false positive, and typical efforts to reduce the number of false positives (increase specificity) usually result in some loss of sensitivity—i.e. the algorithm could miss real events.

While machine learning has become ubiquitous in other pattern matching problems such as image identification and language understanding, machine learning systems are rarely applied to the ECG health data. A reason for this lack of application is significant variations in the ECG data from individual to individual and from time to time of the same individual. It is known for example that ECG data from a healthy and athletically active individual is different from that of a healthy but more sedentary individual. ECG data varies from time to time for an individual and varies based upon activity of the individual. In some cases, patients with identical defects do not have the same ECG waveforms, while in other cases different diseases may result in nearly the same ECG signals. ECG data is temporal. Accurate classification of temporal is still a challenge for machine learning systems such as neural networks including deep learning multilayered neural networks used in other pattern matching applications. One challenge is how to represent the time-varying patterns in a time-independent manner.

Improved methods that maintain the sensitivity while reducing false positive results are needed. The discussions here will demonstrate new techniques applied specifically to electrocardiogram data, but those skilled in the art will readily see the applicability to any other similar timing varying physiological data.

DISCLOSURE OF THE INVENTION

The present invention solves the challenges, and, increases the accuracy and specificity of applying deep learning neural networks to interpreting time varying physiological data. Preprocessing steps and algorithm parameters are used that are specific variously to the diagnoses to be made, the individual whose data is being analyzed, to the specific time interval of the measurements and to the level of activity of the individual while the data is being acquired. In one embodiment the invention includes automatically determining a best algorithm personalized to a particular patient. In another embodiment technician feedback on initial data is used to select a preferred algorithm to be used in subsequent event detection for the particular patient. In another embodiment the invention involves running a Holter scan on the first day of full disclosure ECG from a patient and incorporating that feedback to be used by the algorithm for subsequent event detection over a typical ambulatory monitoring periods run of 10 to 30 days. In another embodiment multiple algorithms are run and the output from each includes a confidence value for the diagnosis and a weighting factor. The combination of confidence intervals and weighting factors are used to select the best diagnosis from amongst a set of diagnoses provided by the multiple algorithms. In another embodiment, technician or physician feedback is used to select weighting factors from a limited portion of the data. In another embodiment the weighting factors are specific to a patient, time or level of activity.

In some embodiments that make use of deep learning neural networks, the raw data is preprocessed specifically for the use of the neural network classification scheme. In some embodiments the preprocessing is specific to the diagnoses being tested. In one embodiment the preprocessing includes acquiring ECG data, calculating the QRS template and then subtracting the template from the live ECG data leaving the P wave for analysis. In a further embodiment the P wave data is subjected to a Fourier Transform resulting in a power spectrum of just P wave data that is submitted to a Deep Learning method. In one embodiment the subtraction of QRS and Fourier transform technique is applied specifically to atrial abnormalities. In another embodiment the subtraction of QRS and Fourier is applied to heart block.

In a non-limiting example of a patient specific embodiment, a patient may have an atrial conduction disorder that results in an irregular heartbeat but is not classified as atrial fibrillation. An algorithm that uses beat-to-beat irregularity to detect atrial fibrillation may provide false positives based on the irregularity. The technician corrects the false positive result presented by the algorithm and provides the correct diagnosis for this patient's rhythm, and that information is then used by the algorithm to correctly identify future episodes of this particular arrhythmia for this particular patient. The specificity of the algorithm for this patient increases, resulting in more accurate diagnosis, fewer false positives, and lower costs. Additionally, in this case, the system runs multiple algorithms on the patient data stream before presenting any events to the technician. The algorithms include one tuned to detect atrial fibrillation with high sensitivity, one used to detect atrial block conditions, one used to detect atrial fibrillation that results in low HR variability and one that uses atrial fibrillation that results in high HR variability. In one embodiment the results of the multiple algorithm result streams are combined and with accuracy and weighting measures to determine the most likely diagnosis to present to the technician. This reduces the number of false positive events the technician has to deal with and lowers the cost of monitoring the patient.

In another embodiment, the technician runs a Holter scan on the first day. The detailed technician corrections, interpretations and identification of "normal" and abnormal portions of the ECG signal are then stored and used by the algorithm system to increase specificity from days 2 through the end of the monitoring period. In one embodiment the output diagnoses of the multiple algorithms are weighted based upon the technician input. In another embodiment the multiple diagnoses outputs are combined by use of the weighting and a confidence value calculated for each algorithm.

In another embodiment the weighting is determined by the algorithm sub-system also monitoring the interpretive statements that the technician applies to events generated by the algorithm and uses this information to more accurately provide interpretations or lists of candidate interpretations in subsequent events that it presents to the technician.

In another embodiment the process involves running multiple, different preprocessing algorithms on a full disclosure data stream or stored full disclosure data and incorporating a voting algorithm to determine which algorithm has the highest specificity, presenting detected events and full disclosure data to a technician, who confirms the algorithms interpretation, incorporating technician feedback into the algorithm to help select the most specific algorithm for a particular patient's morphology and disease state and then continuing to run this personalized algorithm configuration on the patient or the duration of the monitoring period. In another embodiment the full disclosure data is acquired from an ambulatory electrocardiograph.

Another embodiment involves running a specific algorithm on the first day's full disclosure ECG, then incorporating the technician's corrections of algorithms classification. Correction includes changing parameters specific to the algorithm. Parameters are selected such that results of the re-configured personalized algorithm displays increased specificity of events presented to the technician during the remainder of the monitoring period.

MODES FOR CARRYING OUT THE INVENTION

Figure 1:
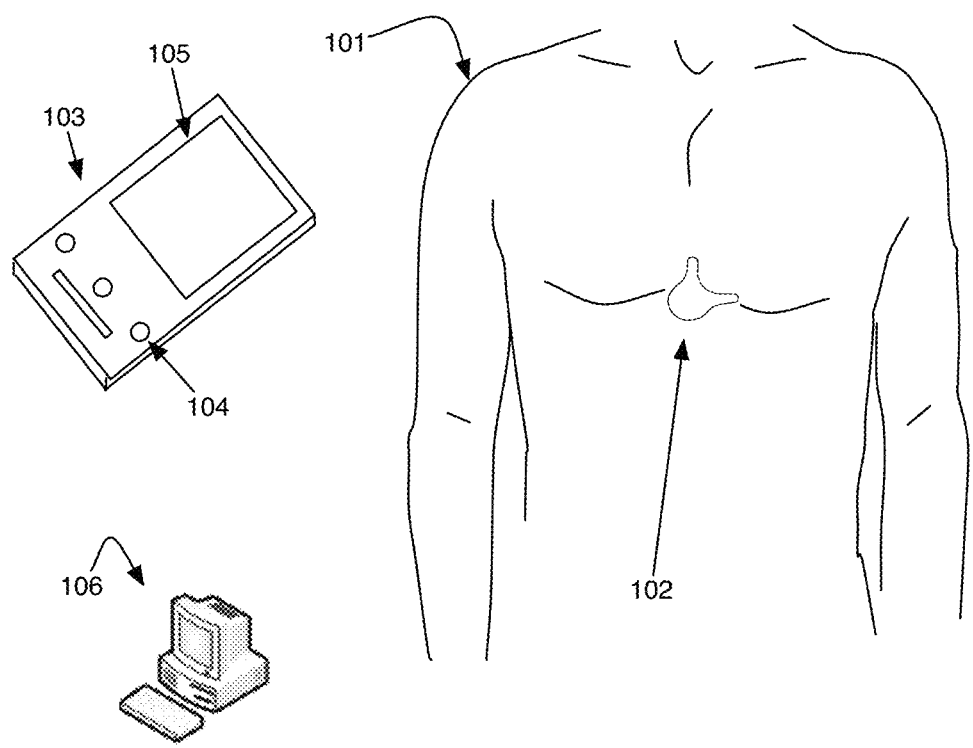
FIG. 1 is a block diagram showing hardware used to practice the invention.

Referring to FIG. 1 systems that may be used to practice the invention are shown. A physiological data acquisition device 102 is attached to a patient 101 and acquires physiological data from the patient. Nonlimiting examples of physiological devices 102 include heart monitors as shown, such as would be used to acquire continuous electrocardiogram (ECG) data from a patient such as in a Holter scan as is known in the industry, electroencephalogram (EEG) data, and devices that acquire movement information such as a respiration monitor, chemistry analysis monitors and temperature monitors. In one embodiment the data acquisition device 102 is connected to a local communication device 103. The local device may include a display 105 and a user interface 104. The data from the data acquisition device 102 is transferred to the local communication device to a computing device 103. The local communication device may further include a computing device programmed for data analysis. In another embodiment the local communication device is used for storage of the acquired data and then transfers the data to a computing device 106 for further analysis. The data transfer between the data acquisition device 102, the local device 103 and the computing device 106 may be through wired or wireless means as are known in the art. In one embodiment the analysis and categorization of the data is done on the computing device 106 that is programmed to use a multi-layer neural network for classifying the acquired data as being indicative of particular diagnoses. In one embodiment preprocessing of the acquired data takes place on the local device 103 and the preprocessed data is sent to the computing device 106 for analysis. The results of the analysis may be relayed back to the local device 103 and displayed to the user or caregiver on the display 105. In one embodiment the local device 103 is a cellular telephone or a tablet with cellular and/or wi-fi communication capabilities. In another embodiment the communication of data is directly between the data acquisition device 102 and the computing device 106 through wired or wireless means.

Figure 2:
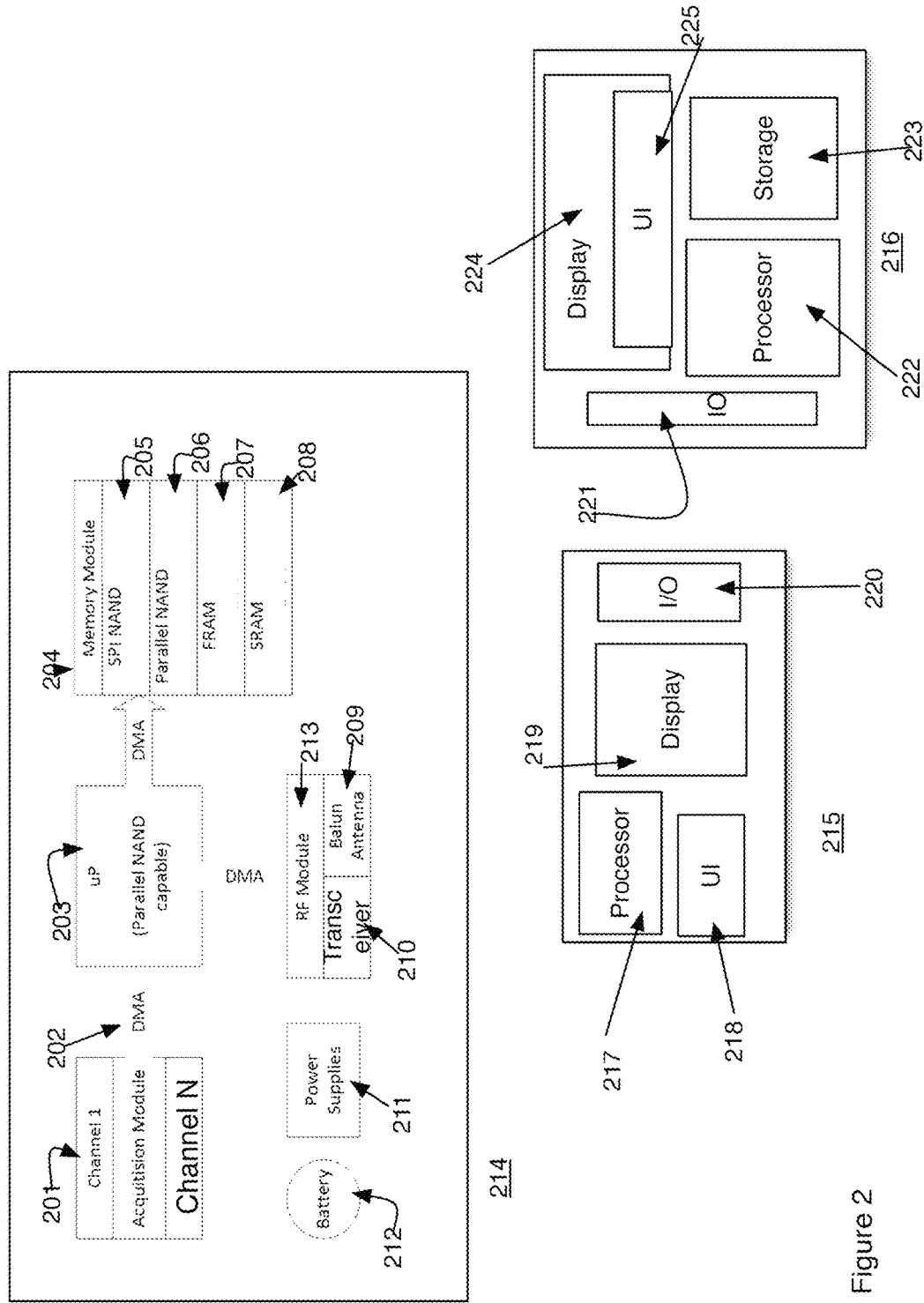
FIG. 2 is a block diagram showing more details of the hardware of FIG. 1.

Further details of the hardware embodiments are shown in FIG. 2. The three devices of FIG. 1 are shown with more detail. The data acquisition device 214, the local communication device 215 and the computing device 216 are shown. The embodiments shown represent the preferred embodiments other embodiments include more or fewer components. The data acquisition device 214 is comprised of a data acquisition module 201. The data acquisition module is attached to the physiological sensor(s) (not shown). Nonlimiting physiological sensors include electrodes for voltage measurements, magnetic sensors, temperature sensors and chemical sensors. In the embodiment shown the data acquisition module is a multichannel data acquisition model. In one embodiment the components of the data acquisition module are as shown in FIG. 2 and there are connections to a plurality of sensors. The data is acquired and transferred 202 to a microprocessor 203 which then stores the data in a memory module 204. The memory module 204 is comprised of at least one of SPI NAND 205, Parallel NAND 206, FRAM 207, and SRAM 208. The microprocessor is programmed to store the data and to send the data through an RF module 213 to the local communication device 215. The RF module is comprised of a transceiver 210 and an antenna 209. The data acquisition device further includes a battery 212 and power supply 211 that supplies regulated power to the other components of the device.

The local communication module 215 is comprised of a processor 217, a user interface 218 a display 219 and an input/output module 220. The input/output module include means for communicating data, program commands and alerts between the data acquisition module 214 and the computing device 216. The display 219 can be comprised of an LCD or LED graphics display as are known in the art or may be as simple as an LED to alert the user or caregiver. The user interface 218 may be a button or keyboard. The processor 217 further includes memory for storage of data and for storage of program steps. The processor may be programmed to send instruction to the data acquisition device to set data acquisition parameters and to start and stop data acquisition. In some embodiments the processor 217 is further programmed to process the acquired data. In one embodiment the processor is programmed to preprocess the acquired data before sending the data on to the computing device 216. In one embodiment the preprocessing is specific to a particular test or diagnoses that is being tested. Details of the preprocessing are discussed below. The communication device further includes a power supply (not shown) to provide power to the components shown. In one embodiment the local communication device 215 is a programmable cellular telephone. In another embodiment the local communication device is a programmable tablet computer or a personal computer. Data acquired from the patient may be stored locally in memory (not shown) in the local communication device 215 and may be processed locally by programs running on the processor 217 that are stored in memory. The programs may be analysis programs using invented methods, described in detail below that provide diagnoses of the patient's condition. The program parameters may be set using the I/O 220 capabilities in communication with the computing device 216 or may be set using the user interface 218. Results may be presented locally to patient and/or caregiver via the display 219. In another embodiment the local processor includes only the ability to acquire data from the data acquisition device 214 and to transmit the data to a central processor 216.

In the preferred embodiment data is sent from the local communication 215 to a computing device 216. The computing device 216 may be located in the proximity of the patient and the communication device 215 or may be centrally located. In a preferred embodiment the patient is an ambulatory patient located remotely from the caregiver and the computing device is located near the caregiver. The computing device is comprised of components typically of a personal or larger computer. The device is comprised of an input output port 221. The IO port may include means for both wired and wireless communication. The computing device includes a processor 222. The processor is programmed using program steps stored in memory 223. The processor may include a graphics processor used for rapid processing of array data such as would be used for pattern recognition through multi-layer neural network programs or deep learning programs as are known in the art. The memory 223 is also used to store data received from the data acquisition device 214 either directly through the IO 221 of the computing device or indirectly from the local communication device 215. The computing device further includes a user interface 225 and a display 224. Not all the components are required. For example, there are computing devices that do not include a display 224 integral to the computing device. In one embodiment both the display and the user interface of the local communication device 215 are used as the display and user interface or the computing device 216.

Figure 3:
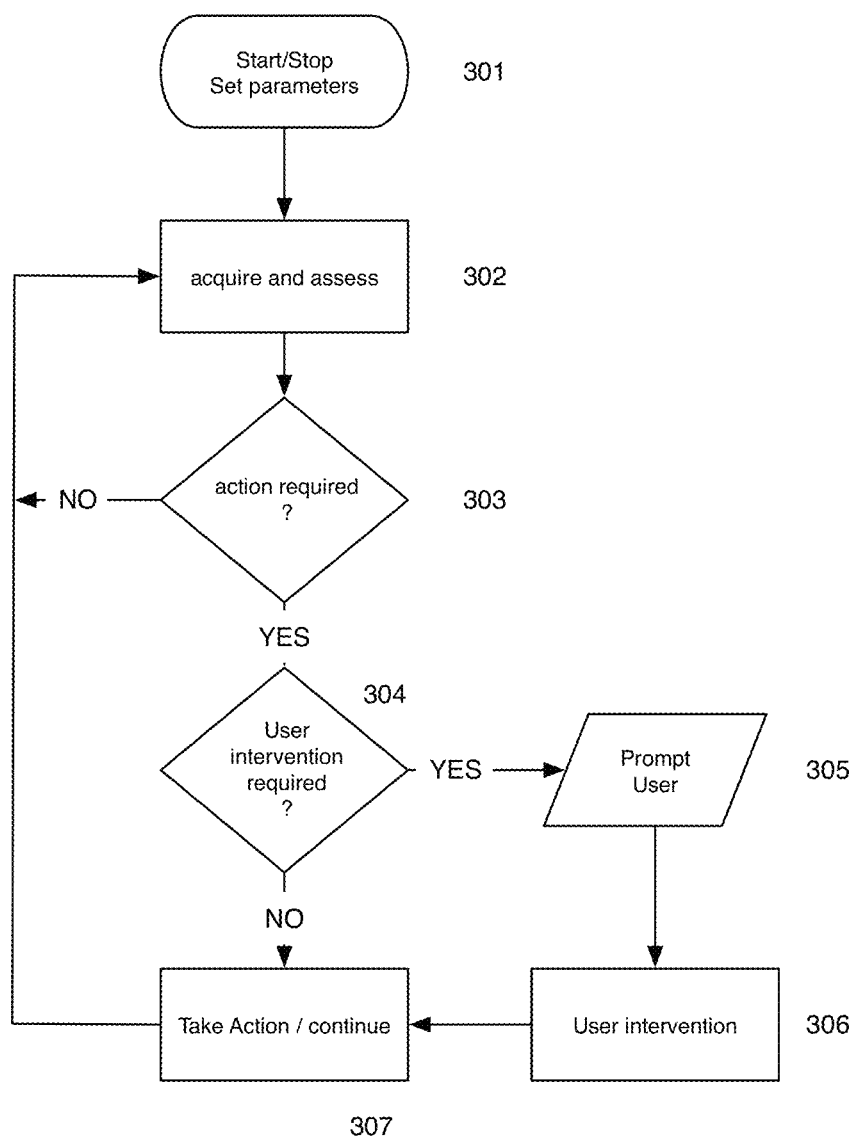
FIG. 3 is a flow chart for a typical physiological data acquisition and analysis process.

Referring now to FIG. 3, flow chart of a general medical diagnosis algorithm is shown. As the process is started 301, parameters for data acquisition and preprocessing are set. Parameters include data acquisition parameters, such as gain settings, length of data acquisition and whether a given measured level in data acquisition will trigger an alert and if so how the alert is delivered, and calculation parameters, including whether raw data or processed data is sent on to to the local communication device or to a computing device or both. The process may be initiated by installation of a battery in the data acquisition device which then automatically activates the device and causes it to link with the local communication device and/or the computing device. Once linked the parameters may be transmitted from the local communication device or the computing device. A set of parameters may be selected via the user interface on either device. In one embodiment activation of the data acquisition device causes an identification index to be sent to the local communication device or the computing device and upon receiving the identification index a parameters menu is displayed on the local communication device for election be the user. The selected parameters from the menu are then uploaded to the data acquisition device to begin data acquisition and assessment 302. Data acquisition means recording signals by the data acquisition device. The signals may be electrical voltages, magnetic signals, and processed signals that may come from an attached analysis device such as for temperature, pH, blood chemistry etc. In the preferred embodiment the signal is an electrocardiogram signal obtained from electrodes attached to the user's/patient's chest. Other similar signals include EEG signals from an array of electrodes attached to the user's/patient's head. The acquired data is transferred to the local communication device and/or local or remote computing device or both.

Assessment 302 includes running a program on the processor of either device to evaluate the acquired signal to determine if it indicates either a normal, healthy, state or if it indicates an abnormal health state for which action might be needed. In the preferred embodiment assessment includes preprocessing off the acquired data and submitting to a multilayer neural network for assessment/classification. In one embodiment the multilayer neural network is a supervised network and the network learns assessment of ECG data using a database of interpreted ECG's. In another embodiment the neural network is unsupervised and classification is learned for the particular user, where different classification states may be indicative of normal heart activity at various activity levels and body positions and abnormal heart activity where a stress indicator accompanies the signal. In another embodiment the output of the neural network is submitted to a classifier that has been trained through using the same neural network to analyze a database of known, interpreted ECG data. A stress indicator may be a signal from an additional sensor such as an accelerometer detecting a fall or unsteady motion or may include a signal from the user that they are experiencing discomfort. A decision 303 as to whether action should be taken ensues. Actions include alerting the user, alerting a caregiver, and/or activating another device. In one embodiment action includes activating a heart pacemaker device. Other actions may include those preselected through the parameters selected at startup 301. Actions may include activating a device when a pattern is recognized in the acquired data. In this case pattern matching/recognition may be through a machine learning neural network algorithm installed on either the local communication device or on the computing device. The computing device may be located either local to the user or remotely. If no action is required, the process continues through acquire and assess. If action is required ("YES" off of decision 303) then a decision 304 is made as to whether user intervention is required. Actions may be preselected to require prompting the user or perhaps to take action without a user prompt. If user intervention is required and a prompt is set in the preselected parameters, user is prompted 305 to take a preselected action or intervention 306 and then the process continues to any further preselected action 307. If not user intervention is required, the path is directly to this latter action 307 and once completed the process continues with data acquisition and processing. The user promptht 305 and the action 307 may include a notification of either the user or the care giver of an unusual event or even a notification that all is OK. Notification parameters, selected earlier 301, include measured physiological values, which if exceeded, would result in notification of the caregiver of an unusual event. Notification parameters include criteria for immediate notification or logging to a report or both. A non-limiting example of a notification parameter includes limits on heart rate, limits on time variability, and limits on the number of arrhythmia events detected over a given time interval. In the preferred embodiment notification is based upon a pattern recognized in the data or detection of a pattern that has not been previously seen in the data. The former might represent using a supervised neural network where the neural network is trained based upon a database of diagnosed ECG's and a parameter is set to take an action if a particular diagnosed condition is detected. In another embodiment the preselected parameter may be set to take an action if a condition is detected that was not previously seen in the learning database. In another embodiment physiological data from the user/patient is collected and analyzed for an initial period with patterns analyzed and classified by a multilayer neural network thereby creating a database of recognized patterns that are unique to the particular user/patient. Subsequent to the learning period, data is acquired from the same user and the neural network system classifies recognized patterns according to the database unique to the user. Preselected parameters are set to take an action based upon either seeing a pattern previously seen and preselected as one in which some action is required or action may be taken based upon the machine learning assessment detecting a new pattern not previously seen with the particular user/patient. Should the measured physiological value be above (or below) a first value, the notification parameter directs the system to log an event for a report. Should the notification parameter be above (or below) a second value the notification parameter directs the system to sound an alarm or otherwise indicate an urgent event. The process may continue in this loop 302-307 indefinitely. A particular action 307 may be to stop data acquisition and assessment in which case the action 307 is also a stop and exit for the process.

Figure 4:
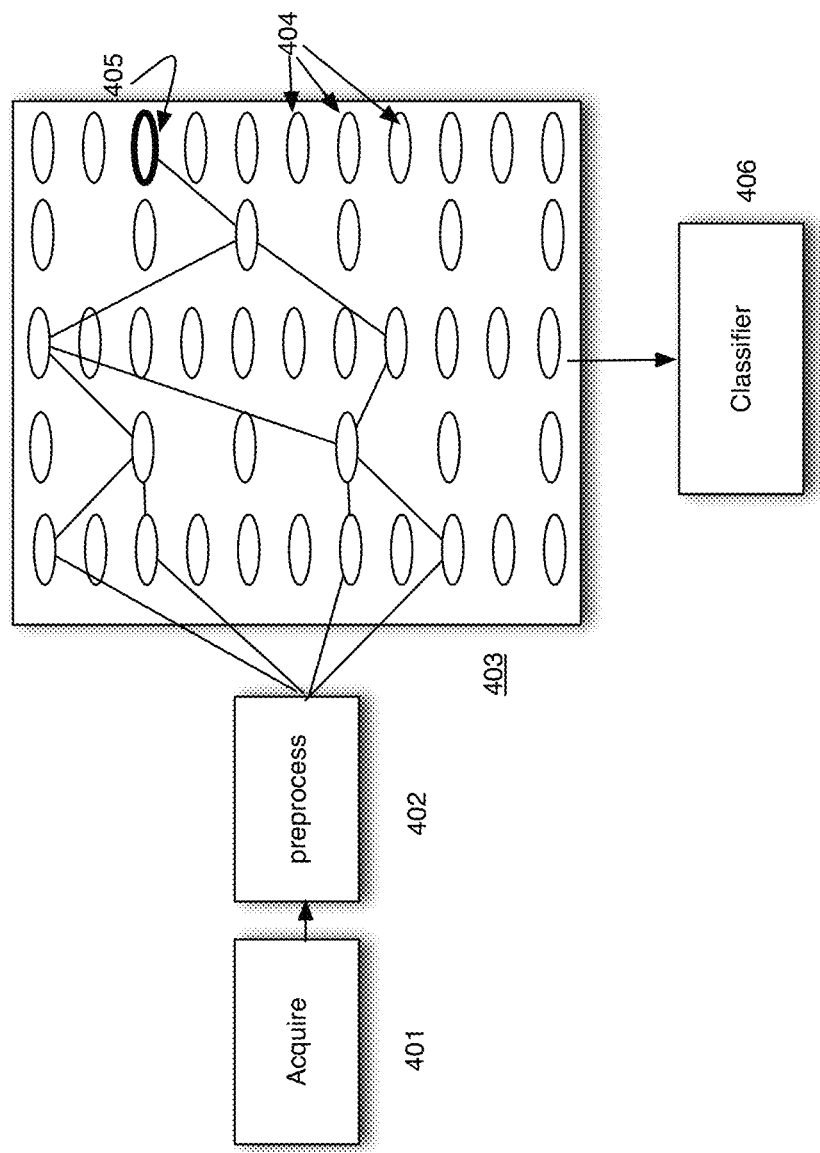
FIG. 4 is a flow chart for a QRS subtraction embodiment.

Referring now to FIG. 4, a block diagram of the deep learning classification process is shown. The Deep learning procedure is comprised of three basic parts: data acquisition and preprocessing 401, 402, neural network analysis and the classifier 406. Raw data is acquired 401. In the preferred embodiment the raw data is an electrocardiogram of voltages versus time. The data is preprocessed 402 before being submitted to a multilayer neural network process 403 for encoding. Preprocessing 402 may include selecting the time region of interest for further analysis, smoothing the data, filtering the data, subtracting features from the data and performing mathematical transforms. In a preferred embodiment the mathematical transform is a wavelet transform. The time region of interest may include all of the data collected over a sampling period, segments of the data that are stepped through for the analysis, a time segment selected on the basis of an external signal. An external signal may include a signal from the user/patient that they are experiencing a health issue. The external signal may be based upon the user/patient activity such as selecting an analysis period when the user is sedentary to reduce muscle induced noise in the data.

The multilayer neural network or deep learning process results in the determination of 10-20 nodes 404, that are automatically created from the ECG features without labels. Classification of the data may result in selection of particular nodes 405 that are unique to or uniquely characteristic of the input data stream. The Neural network thus operating is an unsupervised neural network. When neural network autoencoder 403 is fully trained, the output is a consolidated, smaller number of neurons, and, therefore, input information 401, 402 is "encoded" into lower dimensional space. The encoded data is submitted to a classifier that is trained to recognize the encoded nodes into one or more diagnosis. Nonlimiting exemplary diagnoses include: "normal", "normal for the particular patient" or any one of the many well known in the art symptoms of an abnormal ECG such as fibrillation, flutter, blockage, tachycardia, etc. Once the data is encoded using the neural network encoder, the output is used to teach a new classifier 406 that is taking inputs from the auto-encoder. The classifier 406 is trained on compressed, N-dimensional data. In the preferred embodiment the ECG data of a database is compressed 2-10×. The deep learning process 403 pulls out hidden features of the signal that are not readily observable by a human. Since this new classifier 406 uses only encoded (low-dimensional) inputs, from the encoder 403, it has less parameters and provides better generalization properties (compared to using full input dataset).

Figure 5:
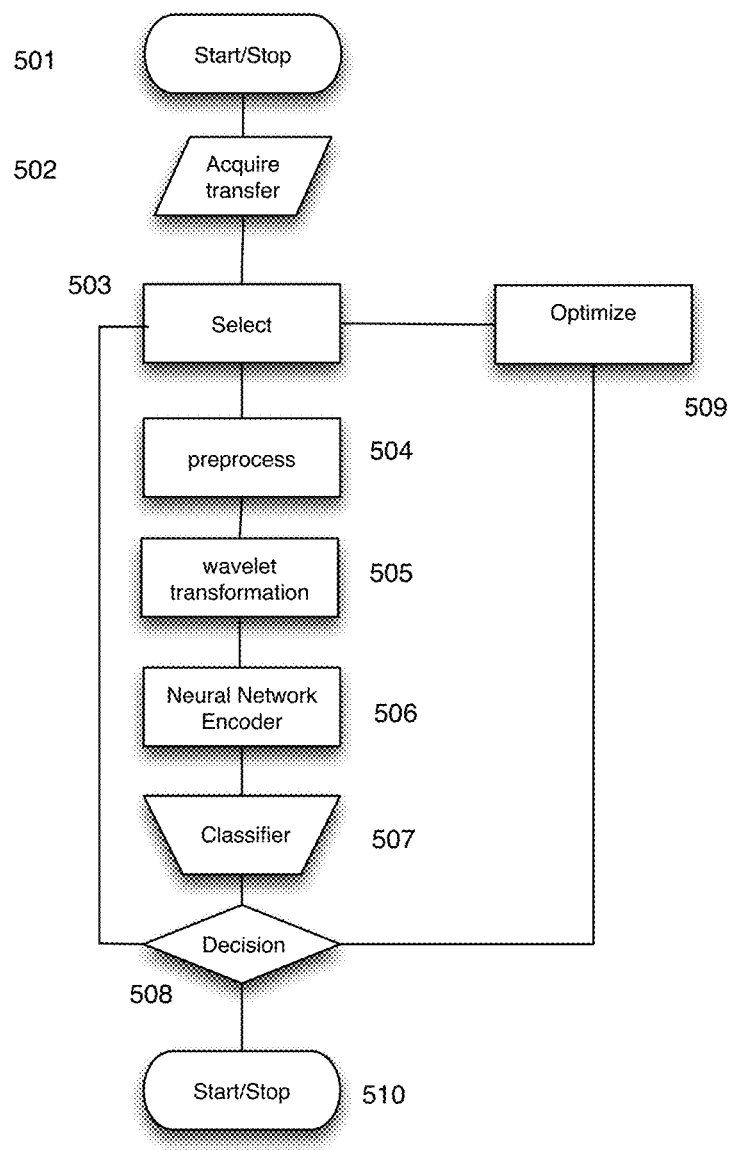
FIG. 5 shows views of data acquired and created using the embodiment of FIG. 4.

In a preferred embodiment, the preprocessing 402 of the biophysical data includes a wavelet transform. The wavelet transform is one selected from: a quadratic spline wavelet and daubechies wavelet. Once transformed the non-local properties of the original ECG data waveform are represented by wavelet coefficients. Encoding in subsequent steps 403, 406 is made more efficient. An additional advantage is that noise in the data usually corresponds to a higher-order wavelets. Separation of a good (representative) signal from the noise is already done by the wavelet transform. FIG. 5 shows a flow chart for the application of wavelet transformation and deep learning to the acquired data. In the preferred mode the data is ECG data. The process is started 501 with data acquisition. The data is acquired 502 from electrodes attached to the user/patient and transferred either directly or indirectly to a computing device for diagnosis. The appropriate portion of the data is selected 503 for analysis. The selection may include all of the data collected or portions of the data based either on preselected parameters. In one embodiment the portion of data is selected based upon an external signal such as a signal from the user or a signal from a secondary sensor.

The data may then be preprocessed 504. Exemplary preprocessing steps include filtering and removing artifacts. Artifacts may include signal disruption through movement of the user or may represent data that is corrupted because of signal interference or faulty connection of electrodes. The data is then subject to a wavelet transformation 505 and then submitted to an unsupervised neural network for encoding 506. The encoded data is then submitted to a classifier that provides a diagnostic result based upon training the classifier using encoded data. In one embodiment the classifier is trained using a database of ECG data that has been previously interpreted and confirmed. In another embodiment the classifier is trained using data specific to the particular user/patient whose data was acquired and analyzed in a controlled environment using the same scheme as described in FIG. 5 but done so under conditions where an expert confirmed the classification of the acquired ECGs. In one embodiment the classifier is trained on data acquired early in a long term ambulatory ECG acquisition process as described below. The classifier provides not just a diagnosis or classification of the ECG data to a particular symptom(s) but also a measure of confidence in the diagnosis. Once the diagnoses are complete through the classifier 507, a decision 508 is made as to whether the process is complete and should stop 510 or whether additional data segments are to be selected and analyzed (route back to select 503) or based upon confidence in the results whether the process should be optimized 509 and analysis of the same or different segments of the data should proceed 503.

In another embodiment the preprocessing is specific to the type of diagnoses being tested. As an example, automatic detection of atrial or SA abnormalities is very challenging task, especially in ambulatory settings where amplitude of noise is usually comparable to the amplitude of p-waves. One of the ways to deal with such data is to detect a sequence of p-waves instead of single p-wave. Such an approach works best if we could estimate the approximate location of every p-wave in a certain time window before the QRS. However, most interesting and clinically significant cases are exactly the ones where the location of a p-wave is not known, for example in the case of a complete heart block. The following system allows to detect complete heart block and atrial flutter in noisy environment.

Figure 6:
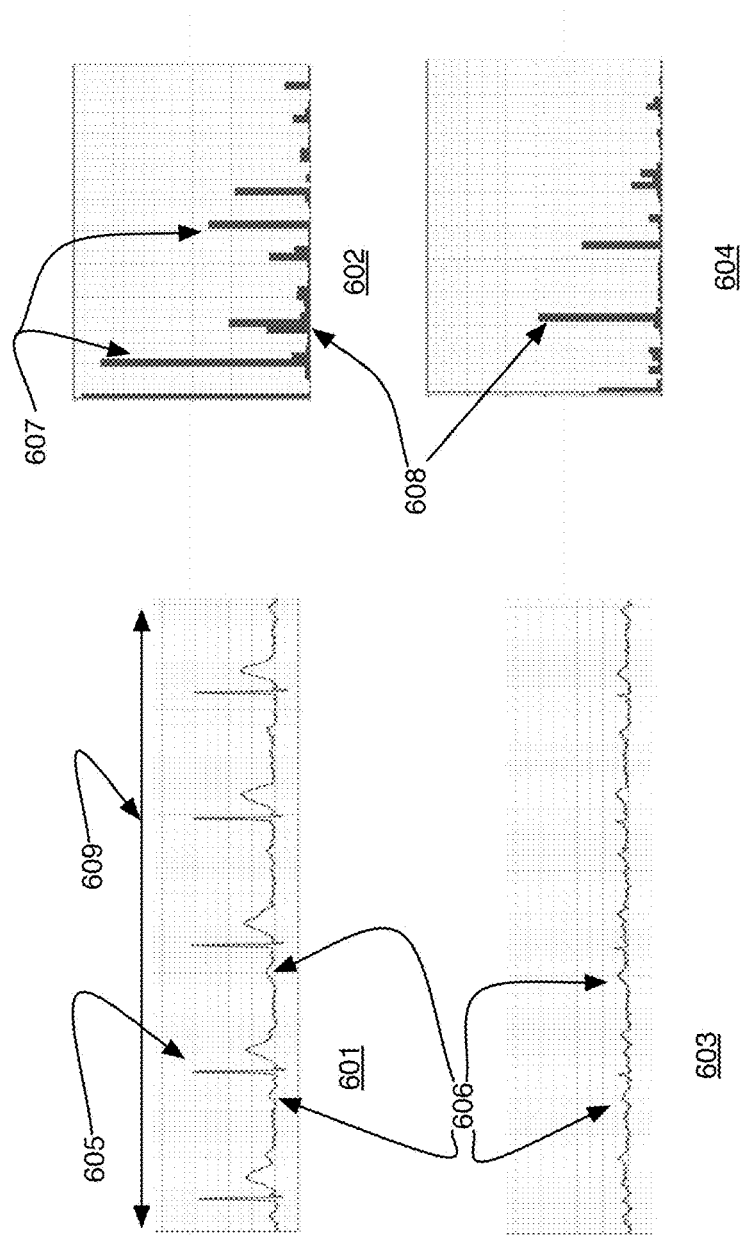
FIG. 6 is a block diagram for a diagnosis specific deep learning process.

The procedure consists of several preprocessing steps. FIG. 6 shows ECG data 601 for typical complete heart block arrhythmia. The QRS complex 605 is easily seen the P waves 606 are less easily detected. Not as part of the process, but for demonstration purposes the Fourier transform spectrum 602 of this ECG is also shown. It is clear, that QRS complexes and harmonics 607 are much larger in amplitude than that for the P wave and harmonics 608. The QRS complex spectrum dominates the power spectrum plot 602. In the diagnosis specific algorithm for P wave blockage the first step is to process this ECG through a QRS detector and calculate a QRS waveform template as is known in the art. The calculated QRS template (including T-wave) is subtract from every beat in the region of interest 609 of the original ECG data. The result of such subtraction 603 shows result of first step in pre-processing: QRS complexes and T-waves are removed using the QRS template. There is some residual noise from the QRS complexes. However, we don't need to remove QRS's perfectly, we just need to significantly reduce their amplitude. The P waves 606 are seen to remain in the data. A Fourier transform 604 and the resulting power spectrum has now p-wave frequency and their harmonics 608 shown much clearer, and their identification could be done much more reliably. The power spectrum 604 is then submitted to the multilayer neural network encoding and classifier. The example shown in the FIG. 6 uses initial data 601 previously diagnosed as indicative of blockage. In practice the subtraction and Fourier transform would be applied to ECG data prior to a diagnosis. In a preferred embodiment the procedure is part of a multiple parallel process for ECG diagnoses. In one path the data is treated as discussed in FIGS. 4 and 5 using the wavelet transform as preprocessing and in parallel the same data would use the QRS subtraction and Fourier transform procedure. Preprocessing steps that enhance the confidence of particular diagnoses are run in parallel. The QRS subtraction and Fourier transform is one of a nonlimiting example.

In another embodiment a preprocess specific for Atrial flutter is used. The procedure is the same as that described above for the heart block arrhythmia except that the weightings in the encoding are adjusted such that the power spectrum of those waves at a higher frequency indicative of flutter are given higher weighting. In this procedure the same preprocess is used with two separate encoding processes. One encoding process specific to atrial blockage and the other specific to atrial flutter.

Figure 7:
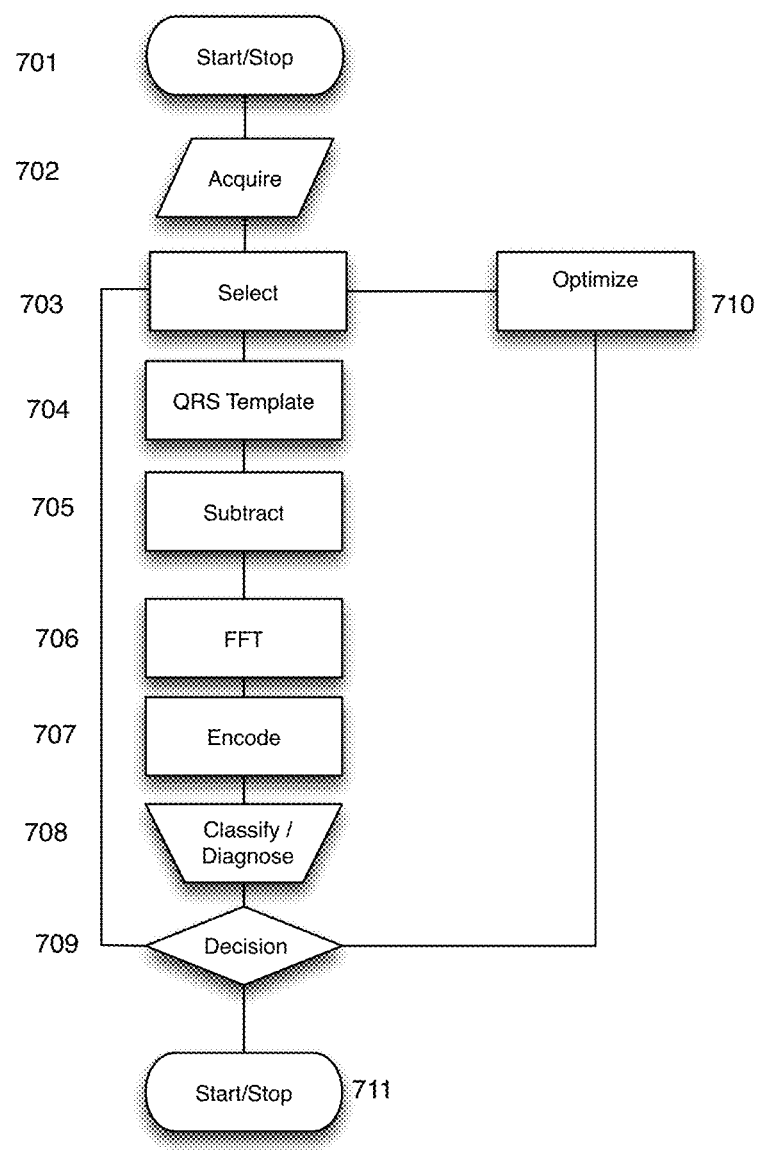
FIG. 7 is a flow chart for the process of FIG. 6.

FIG. 7 shows a flow chart for a preprocess specific diagnosis procedure. The process is initiated 701 and data is collected 702 and transferred either directly or indirectly to a computing device. A region of interest is selected 703. The selection is as already discussed above. In addition, the region of interest may be selected on the basis of those portions of the data likely to be indicative of the particular diagnosis for which the preprocess is targeted. That is in one embodiment the region is selected where the user/patient is showing symptoms indicative of the target diagnosis. In the example the region is selected where the patient is showing symptoms of blockage and the preprocess and encoding/classifier are those trained for blockage. In another example the region is selected where the patient is showing signs of atrial flutter and preprocess and encoding/classifier are those trained/weighted specifically for atrial flutter. A QRS template is then calculated 704 from the data within the region of interest and the QRS template is subtracted 705 from every instance of QRS wave within the data in the region of interest. A Fast Fourier transform (FFT) is applied 706 to the data resulting in a power spectrum for the repeating waves in the ECG other than the QRS complex. The Fourier transform data is submitted to encoding 707 through a multi-layer neural network and the results are passed through a classifier 708 for a diagnosis. Once diagnosed the system decides 709 based either upon the diagnosis results and confidence in those results or upon preselected parameters to either end the process 711, proceed to analysis of an additional region of the ECG data 703 or to optimize the process by adjusting parameters 710 and then analyze either the same or a different selected region of the ECG data 703. The process may continue through the loop until all of the data has been analyzed or a preselected parameter such as confidence in the diagnosis has been reached.

Figure 8:
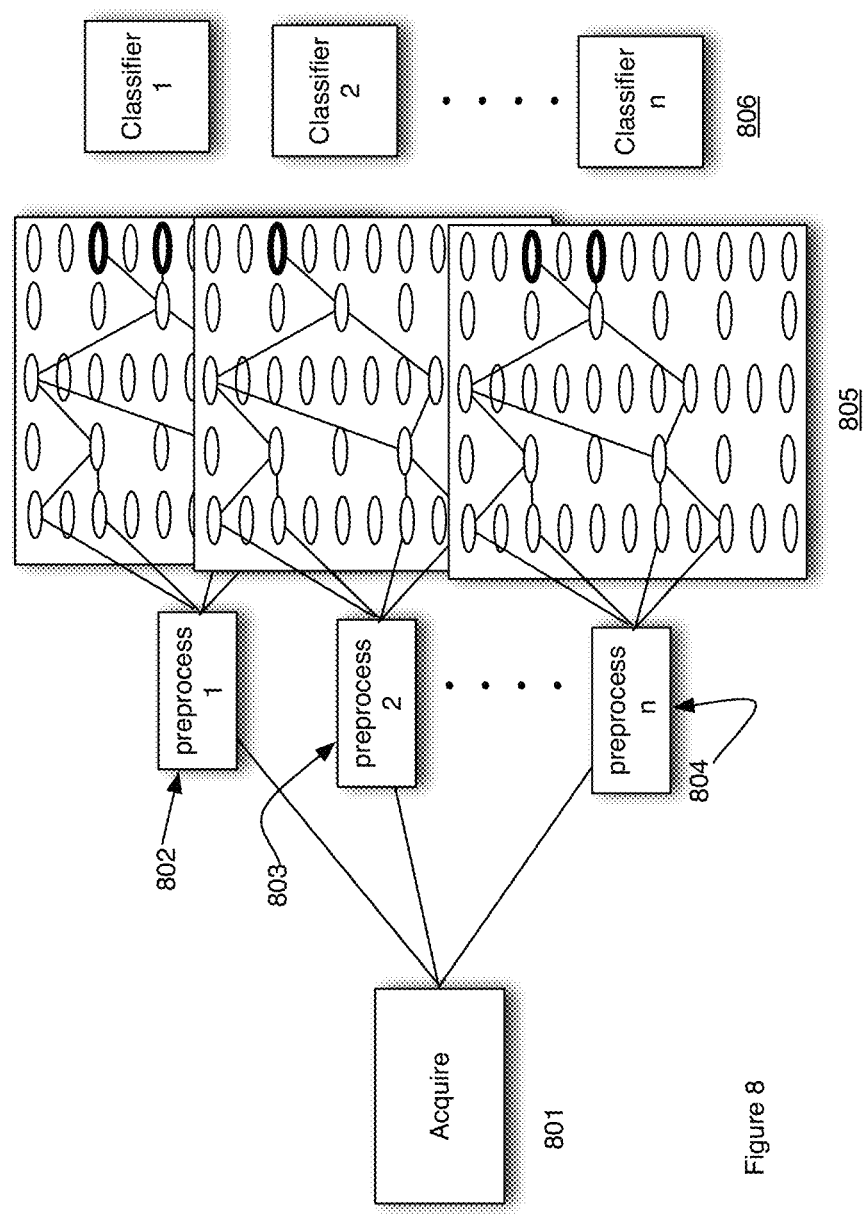
FIG. 8 is a block diagram for a multiple parallel deep learning neural network process using the embodiments of FIGS. 3-7.
Figure 9:
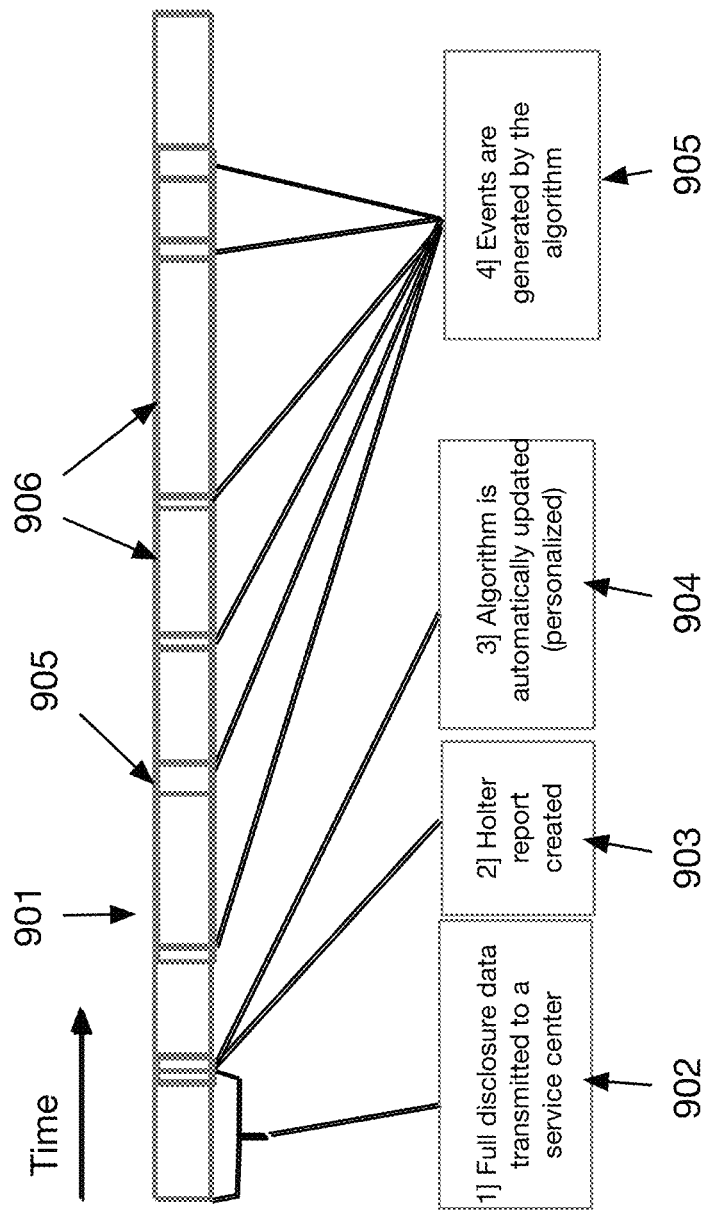
FIG. 9 is a time line for preparing and running the processes of FIGS. 3-8.

In another embodiment, shown in FIG. 8, multiple deep learning procedure are run in parallel where each of the individual parallel processes may include preprocessing, encoding and classifiers that are tailored for improved results for individual diagnoses. Data is acquired 801 and transferred to a computing device or perhaps multiple computing devices. The data is split into particular preprocessing steps 802, 803, 804 where on or several of the preprocessing steps may be tailored for specific diagnoses. In a nonlimiting example preprocess step 1 may include a wavelet transformation, preprocess 2 may include calculating a QRS template and subtracting the template to remove QRS bands, both as previously discussed. The preprocessed data is submitted to individual encoders 805 which then submit encoded data to classifiers 806 where the encoders and the classifiers may further be tailored to specific diagnoses tasks again as already discussed. The process may run in parallel as shown or in another embodiment the individual preprocessing, encoding and classifiers are run in parallel. In another embodiment the first preprocess 802 is a general procedure/diagnostic procedure using a wavelet transformation and the diagnostic results of the Classifier 1 are used to decide whether other specific preprocesses should be run on the same data set.

In another embodiment a timeline 901 for a ECG analysis procedure is shown. Full disclosure data is recorded and analyzed 902 and a Holter report is generated 903. Algorithms, weightings for encoders and preprocessing procedures for data are selected 904. The algorithms, weightings and preprocessing procedures are thereby customized to the particular user. Data is then continuously collected and analyzed according to one or all of the procedures already described thereby creating events 905. The events may be reported to the user, reported to the caregiver or used to initiate an action to change the analysis for future events or to initiate an action by another device. In another embodiment the events are created at preselected intervals 906. In one embodiment the intervals are selected based upon the initial analysis 904. In another embodiment the intervals 906 are updated based upon events 905.

SUMMARY

Devices and methods are described that provide improved diagnosis from the processing of physiological data. The methods include use of transforms prior to submitting the data to a multiple level neural network. In one embodiment for ECG analysis, a template is used to subtract data that is not pertinent to the diagnosis and then a Fourier transform is applied to the time series data. Examples are shown with applications to electrocardiogram data, but the methods taught are applicable to many types of physiological data.

Those skilled in the art will appreciate that various adaptations and modifications of the preferred embodiments can be configured without departing from the scope and spirit of the invention. Therefore, it is to be understood that the invention may be practiced other than as specifically described herein, within the scope of the appended claims.

What is claimed is:

1. A system for providing a health diagnosis, to a medical practitioner, from electrocardiogram data acquired from a patient over a time period, said electrocardiogram data including a plurality of heartbeats, and, each heartbeat including PQRST wave data, and, said system comprising:
   a) a sensor for measuring the electrocardiogram data over the time period, and, storing the electrocardiogram data, and, transferring the electrocardiogram data to a computing device,
   b) the computing device further programmed to:
      i) perform a mathematical transform on the electrocardiogram data, where the mathematical transform is at least one selected, by the medical practitioner, from:

(1) a wavelet transform,
(2) creating a template of QRS data from the electrocardiogram data and subtracting the template of QRS data from each of the plurality of heartbeats,
(3) a Fourier transform, and
where the mathematical transform is selected on the basis of a health diagnosis to be tested, thereby producing transformed physiological data, and ii) encode the transformed physiological data using a multiple layer neural network, thereby producing an encoded output, iii) classify the encoded output using a classifier that has been previously trained using a library of time varying physiological data with confirmed diagnoses, thereby producing a classified output, c) wherein the classified output is the health diagnosis for the patient.

2. The system of claim 1 wherein the library of time varying physiological data with confirmed diagnoses is produced by collecting and interpreting time varying physiological data from the patient in a first time period, said first time period occurring prior to the time period of claim 1, and wherein the confirmed diagnoses are produced by a human technician.

3. The system of claim 1 wherein the mathematical transform includes: creating a template of QRS data from the electrocardiogram data and subtracting the template of QRS data from each of the plurality of heartbeats, and, a Fourier transform, and, the health diagnosis to be tested is P wave blockage.

4. The system of claim 3 wherein the library of time varying physiological data with confirmed diagnoses is produced by collecting and interpreting time varying physiological data from the patient in a first time period, said first time period occurring prior to the time period of claim 1, and wherein the confirmed diagnoses are produced by a human technician.

5. The system of claim 1 wherein the mathematical transform includes: creating a template of QRS data from the electrocardiogram data and subtracting the template of QRS data from each of the plurality of heartbeats, and, a Wavelet transform, and, the health diagnosis to be tested is P wave flutter.

6. The system of claim 5 wherein the library of time varying physiological data with confirmed diagnoses is produced by collecting and interpreting time varying physiological data from the patient in a first time period, said first time period occurring prior to the time period of claim 1, and wherein the confirmed diagnoses are produced by a human technician.

* * * * *